US008386000B2

(12) United States Patent
McKenna

(10) Patent No.: US 8,386,000 B2
(45) Date of Patent: Feb. 26, 2013

(54) SYSTEM AND METHOD FOR PHOTON DENSITY WAVE PULSE OXIMETRY AND PULSE HEMOMETRY

(75) Inventor: Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1184 days.

(21) Appl. No.: 12/241,160

(22) Filed: Sep. 30, 2008

(65) Prior Publication Data

US 2010/0081899 A1  Apr. 1, 2010

(51) Int. Cl.
*A61B 5/1455* (2006.01)
(52) U.S. Cl. .......................... 600/323; 600/310; 600/476
(58) Field of Classification Search .................. 600/310, 600/322, 323, 336, 473, 476
See application file for complete search history.

(56) References Cited

U.S. PATENT DOCUMENTS

| | | | |
|---|---|---|---|
| 3,638,640 A | 2/1972 | Shaw | |
| 4,223,680 A | 9/1980 | Jöbsis | |
| 4,281,645 A | 8/1981 | Jöbsis | |
| 4,321,930 A | 3/1982 | Jöbsis et al. | |
| 4,714,341 A | 12/1987 | Hamaguri et al. | |
| 4,805,623 A | 2/1989 | Jöbsis | |
| 4,807,631 A | 2/1989 | Hersh et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,088,493 A | 2/1992 | Giannini et al. | |
| 5,119,815 A | 6/1992 | Chance | |
| 5,122,974 A | 6/1992 | Chance | |
| 5,167,230 A | 12/1992 | Chance | |
| 5,187,672 A | 2/1993 | Chance et al. | |
| 5,190,038 A | 3/1993 | Polson et al. | |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |

(Continued)

FOREIGN PATENT DOCUMENTS

| | | |
|---|---|---|
| AU | 732799 B2 | 5/2001 |
| DE | 69123448 | 5/1997 |

(Continued)

OTHER PUBLICATIONS

D.J. Pine, et al.; "Diffusing-Wave Spectroscopy," *The American Physical Society*, vol. 60, No. 12, Mar. 1988, pp. 1134-1137.

(Continued)

*Primary Examiner* — Eric Winakur
(74) *Attorney, Agent, or Firm* — Fletcher Yoder

(57) ABSTRACT

Present embodiments are directed to a system and method capable of modulating light at a modulation frequency, wherein the modulation frequency is somewhere above about 50 MHz and below about 3 GHz, to generate photon density waves in a medium, detecting relative amplitude changes and phase shifts in the photon density waves, and detecting and graphically indicating a physiologic value related to scattering particles in the medium based on the phase shifts.

20 Claims, 5 Drawing Sheets

U.S. PATENT DOCUMENTS

| | | | |
|---|---|---|---|
| 5,279,295 A | 1/1994 | Martens et al. |
| 5,297,548 A | 3/1994 | Pologe |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,497,769 A | 3/1996 | Gratton et al. |
| 5,553,614 A | 9/1996 | Chance |
| 5,555,885 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Kuenstner |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,831,598 A | 11/1998 | Kauffert et al. |
| 5,842,981 A | 12/1998 | Larsen et al. |
| 5,871,442 A | 2/1999 | Madarasz et al. |
| 5,873,821 A | 2/1999 | Chance et al. |
| 5,899,865 A | 5/1999 | Chance |
| 5,920,263 A | 7/1999 | Huttenhoff et al. |
| 5,995,855 A | 11/1999 | Kiani et al. |
| 5,995,856 A | 11/1999 | Mannheimer et al. |
| 5,995,859 A | 11/1999 | Takahashi |
| 6,011,986 A | 1/2000 | Diab et al. |
| 6,058,324 A * | 5/2000 | Chance ................... 600/473 |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,192,261 B1 | 2/2001 | Gratton et al. |
| 6,230,035 B1 | 5/2001 | Aoyagi et al. |
| 6,246,892 B1 | 6/2001 | Chance |
| 6,266,546 B1 | 7/2001 | Steuer et al. |
| 6,285,895 B1 | 9/2001 | Ristolainen et al. |
| 6,312,393 B1 | 11/2001 | Abreu |
| 6,322,515 B1 | 11/2001 | Goor et al. |
| 6,352,502 B1 | 3/2002 | Chaiken et al. |
| 6,353,750 B1 | 3/2002 | Kimura et al. |
| 6,397,091 B2 | 5/2002 | Diab et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,516,209 B2 | 2/2003 | Cheng et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,615,064 B1 | 9/2003 | Aldrich |
| 6,618,042 B1 | 9/2003 | Powell |
| 6,622,095 B2 | 9/2003 | Kobayashi et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,684,090 B2 | 1/2004 | Ali et al. |
| 6,690,958 B1 | 2/2004 | Walker et al. |
| 6,697,658 B2 | 2/2004 | Al-Ali |
| 6,708,048 B1 | 3/2004 | Chance |
| 6,711,424 B1 | 3/2004 | Fine et al. |
| 6,711,425 B1 | 3/2004 | Reuss |
| 6,714,245 B1 | 3/2004 | Ono |
| 6,731,274 B2 | 5/2004 | Powell |
| 6,785,568 B2 | 8/2004 | Chance |
| 6,793,654 B2 | 9/2004 | Lemberg |
| 6,801,648 B2 | 10/2004 | Cheng |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,850,053 B2 | 2/2005 | Daalmans et al. |
| 6,859,658 B1 | 2/2005 | Krug |
| 6,863,652 B2 | 3/2005 | Huang et al. |
| 6,873,865 B2 | 3/2005 | Steuer et al. |
| 6,889,153 B2 | 5/2005 | Dietiker |
| 6,898,451 B2 | 5/2005 | Wuori |
| 6,939,307 B1 | 9/2005 | Dunlop |
| 6,947,780 B2 | 9/2005 | Scharf |
| 6,949,081 B1 | 9/2005 | Chance |
| 6,961,598 B2 | 11/2005 | Diab |
| 6,983,178 B2 | 1/2006 | Fine et al. |
| 6,993,371 B2 | 1/2006 | Kiani et al. |
| 6,996,427 B2 | 2/2006 | Ali et al. |
| 7,006,676 B1 | 2/2006 | Zeylikovich et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,035,697 B1 | 4/2006 | Brown |
| 7,047,056 B2 | 5/2006 | Hannula et al. |
| 7,090,648 B2 | 8/2006 | Sackner et al. |
| 7,127,278 B2 | 10/2006 | Melker et al. |
| 7,162,306 B2 | 1/2007 | Caby et al. |
| 7,164,938 B2 | 1/2007 | Geddes et al. |
| 7,209,775 B2 | 4/2007 | Bae et al. |
| 7,236,811 B2 | 6/2007 | Schmitt |
| 7,263,395 B2 | 8/2007 | Chan et al. |
| 7,272,426 B2 | 9/2007 | Schmid |
| 7,330,746 B2 | 2/2008 | Demuth et al. |
| 7,373,193 B2 | 5/2008 | Al-Ali et al. |
| 7,375,347 B2 | 5/2008 | Colvin et al. |
| 7,378,954 B2 | 5/2008 | Wendt |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |

| | | |
|---|---|---|
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0197583 A1 | 9/2005 | Chance |
| 2005/0203357 A1 | 9/2005 | Debreczeny et al. |
| 2005/0209516 A1 | 9/2005 | Fraden |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058595 A1 | 3/2006 | Herrmann |
| 2006/0058683 A1 | 3/2006 | Chance |
| 2006/0063995 A1 | 3/2006 | Yodh et al. |
| 2006/0064024 A1 | 3/2006 | Schnall |
| 2006/0122475 A1 | 6/2006 | Balberg et al. |
| 2006/0129037 A1 | 6/2006 | Kaufman et al. |
| 2006/0129038 A1 | 6/2006 | Zelenchuk et al. |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0247506 A1 | 11/2006 | Balberg et al. |
| 2006/0258921 A1 | 11/2006 | Addison et al. |
| 2007/0093702 A1 | 4/2007 | Yu et al. |
| 2008/0139908 A1 | 6/2008 | Kurth |
| 2008/0177163 A1 | 7/2008 | Wang et al. |
| 2008/0200823 A1 | 8/2008 | Cho et al. |
| 2008/0312533 A1 | 12/2008 | Balberg et al. |

FOREIGN PATENT DOCUMENTS

| | | |
|---|---|---|
| DE | 19640807 | 9/1997 |
| EP | 0194105 | 9/1986 |
| JP | 3124073 | 5/1991 |
| JP | 3170866 | 7/1991 |
| JP | 3238813 | 10/1991 |
| JP | 4191642 | 7/1992 |
| JP | 4332536 | 11/1992 |
| JP | 5049624 | 3/1993 |
| JP | 7124138 | 5/1995 |
| JP | 10216115 | 9/1998 |
| JP | 11019074 | 1/1999 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004194908 | 7/2004 |
| JP | 2004202190 | 7/2004 |
| JP | 2004248819 | 9/2004 |
| JP | 2004290544 | 10/2004 |
| JP | 2004290545 | 10/2004 |
| WO | WO9101678 | 2/1991 |
| WO | WO9200513 | 1/1992 |
| WO | WO9221281 | 12/1992 |
| WO | WO9309711 | 5/1993 |
| WO | WO9313706 A2 | 7/1993 |
| WO | WO93/16629 | 9/1993 |
| WO | WO9403102 | 2/1994 |
| WO | WO9512349 | 5/1995 |
| WO | WO9749330 | 12/1997 |
| WO | WO9817174 | 5/1998 |
| WO | WO98/42249 | 10/1998 |
| WO | WO98/42251 | 10/1998 |
| WO | WO9843071 | 10/1998 |
| WO | WO9932030 | 7/1999 |
| WO | WO0021438 | 4/2000 |
| WO | WO0140776 | 6/2001 |
| WO | WO03077750 | 9/2003 |
| WO | WO2004010844 | 2/2004 |
| WO | WO2005009221 | 2/2005 |
| WO | WO2005064314 A1 | 7/2005 |
| WO | WO2007051066 | 5/2007 |

OTHER PUBLICATIONS

D.J. Pine, et al.; "Diffusing-wave spectroscopy: dynamic light scattering in the multiple scattering limit," *J. Phys. France*, vol. 51, Sep. 1990, pp. 2101-2127.

X.L. Wu, et al.; "Diffusing-wave spectroscopy in a shear flow," *J. Opt. Soc. Am. B.*, vol. 7, No. 1, Jan. 1990, pp. 15-20.

J.M. Schmitt, et al.; "Interference of diffusive light waves," *J. Opt. Soc. Am. A.*, vol. 9, No. 10 (Oct. 1992), pp. 1832-1843.

Aoyagi, T., et al.; "Analysis of Motion Artifacts in Pulse Oximetry," Japanese Society ME, vol. 42, p. 20 (1993) (Article in Japanese—contains English summary of article).

D.A. Weitz, et al.; "Diffusing-Wave Spectroscopy: The Technique and Some Applications," *Physica Scripta*, vol. T49, 1993, pp. 610-621.

Barreto, A.B., et al.; "Adaptive Cancelation of Motion artifact in Photoplethysmographic Blood Volume Pulse Measurements for Exercise Evaluation," IEEE-EMBC and CMBEC—Theme 4: Signal Processing, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," Journal of clinical Monitoring, vol. 13, pp. 109-113 (1997).

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Poets, C. F., et al.; "Detection of movement artifact in recorded pulse oximeter saturation," Eur. J. Pediatr.; vol. 156, pp. 808-811 (1997).

Masin, Donald I., et al.; "Fetal Transmission Pulse Oximetry," Proceedings 19th International Conference IEEE/EMBS, Oct. 30-Nov. 2, 1997; pp. 2326-2329.

Nijland, Roel, et al.; "Validation of Reflectance Pulse Oximetry: An Evaluation of a new Sensor in Piglets," Journal of Clinical Monitoring, vol. 13, pp. 43-49 (1997).

Nogawa, Masamichi, et al.; "A New Hybrid Reflectance Optical Pulse Oximetry Sensor for Lower Oxygen Saturation Measurement and for Broader Clinical Application," SPIE, vol. 2976, pp. 78-87 (1997).

Mannheimer, Paul D., et al.; "Wavelength Selection for Low-Saturation Pulse Oximetry," IEEE Transactions on Biomedical Engineering, vol. 44, No. 3, pp. 148-158 (Mar. 1997).

Buschman, J.P., et al.; "Principles and Problems of Calibration of Fetal Oximeters," Biomedizi nische Technik, vol. 42, pp. 265-266 (1997).

Leahy, Martin J., et al.; "Sensor Validation in Biomedical Applications," IFAC Modelling and Control in Biomedical Systems, Warwick, UK; pp. 221-226 (1997).

Barreto, Armando B., et al.; "Adaptive LMS Delay Measurement in dual Blood Volume Pulse Signals for Non-Invasive Monitoring," IEEE, pp. 117-120 (1997).

East, Christine E., et al.; "Fetal Oxygen Saturation and Uterine Contractions During Labor," American Journal of Perinatology, vol. 15, No. 6, pp. 345-349 (Jun. 1998).

Hayes, Matthew J., et al.; "Quantitative evaluation of photoplethysmographic artifact reduction for pulse oximetry," SPIE, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, p. 3072-3075, 1998.

Hayes, Matthew J., et al.; "Artifact reduction in photoplethysmography," Applied Optics, vol. 37, No. 31, pp. 7437-7446 (Nov. 1998).

S.E. Skipetrov, et al.; "Diffusing-wave spectroscopy in randomly inhomogeneous media with spatially localized scatterer flows," *Journal of Experimental and Theoretical Physics*, vol. 86, No. 4, Apr. 1998, pp. 661-665.

Such, Hans Olaf; "Optoelectronic Non-invasive Vascular Diagnostics Using multiple Wavelength and Imaging Approach," Dissertation, (1998).

Lutter, N., et al.; "Comparison of Different Evaluation Methods for a Multi-wavelength Pulse Oximeter," Biomedizinische Technik, vol. 43, (1998).

Z.L. Wu, et al.; "Laser modulated scattering as a nondestructive evaluation tool for defect inspection in optical materials for high power laser applications," *Optics Express*, vol. 3, No. 10; Nov. 1998, pp. 376-383.

Todd, Bryan, et al.; "The Identification of Peaks in Physiological Signals," Computers and Biomedical Research, vol. 32, pp. 322-335 (1999).

G. Popescu, et al.; "Optical path-length spectroscopy of wave propagation in random media," *Optics Letters*, vol. 24, No. 7, Apr. 1999, pp. 442-444.

Rhee, Sokwoo, et al.; "Design of a Artifact-Free Wearable Plethysmographic Sensor," Proceedings of the First joint BMES/EMBS Conference, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," Journal of clinical Anestesia, vol. 11, pp. 192-195 (1999).

Kaestle, S.; "An Algorithm for Reliable Processing of Pulse Oximetry Signals Under strong Noise Conditions," Dissertation Book, Lubeck University, Germany (1999).

Seelbach-Göbel, Birgit, et al.; "The prediction of fetal acidosis by means of intrapartum fetal pulse oximetry," Am J. Obstet. Gynecol., vol. 180, No. 1, Part 1, pp. 73-81 (1999).

Goldman, Julian M.; "Masimo Signal Extraction Pulse Oximetry," Journal of Clinical Monitoring and Computing, vol. 16, pp. 475-483 (2000).

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Al. N. Korolevich, et al.: "Experimental study of the potential use of diffusing wave spectroscopy to investigate the structural characteristics of blood under multiple scattering," *Bioelectrochemistry*, vol. 52, 2000, pp. 223-227.

V. Ntziachristos, et al.; "Oximetry based on diffuse photon density wave differentials," *Am. Assoc. Phys. Med.*, vol. 27, No. 2, Feb. 2000, pp. 410-521.

Yao, Jianchu, et al.; "Design of a Plug-and-Play Pulse Oximeter," Proceedings of the Second Joint EMBS/BMES Conference, Houston, Texas, Oct. 23-26, 2002; pp. 1752-1753.

Kaestle, S.; "Determining Artefact Sensitivity of New Pulse Oximeters in Laboratory Using Signals Obtained from Patient," Biomedizinische Technik, vol. 45 (2000).

Cysewska-Sobusaik, Anna; "Metrological Problems With noninvasive Transillumination of Living Tissues," Proceedings of SPIE, vol. 4515, pp. 15-24 (2001).

Belal, Suliman Yousef, et al.; "A fuzzy system for detecting distorted plethysmogram pulses in neonates and paediatric patients," Physiol. Meas., vol. 22, pp. 397-412 (2001).

Hayes, Matthew J., et al.; "A New Method for Pulse Oximetry Possessing Inherent Insensitivity to Artifact," IEEE Transactions on Biomedical Engineering, vol. 48, No. 4, pp. 452-461 (Apr. 2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Gehring, Harmut, et al.; "The Effects of Motion Artifact and Low Perfusion on the Performance of a New Generation of Pulse Oximeters in Volunteers Undergoing Hypoxemia," Respiratory Care, Vo. 47, No. 1, pp. 48-60 (Jan. 2002).

Jopling, Michae W., et al.; "Issues in the Laboratory Evaluation of Pulse Oximeter Performance," Anesth Analg, vol. 94, pp. S62-S68 (2002).

Lutter, N., et al.; "Accuracy of Noninvasive Continuous Blood Pressure; Measurement Utilising the Pulse Transit Time," Journal of clinical Monitoring and Computing, vol. 17, Nos. 7-8, pp. 469 (2002).

Gostt, R., et al.; "Pulse Oximetry Artifact Recognition Algorithm for Computerized Anaesthetic Records," Journal of Clinical Monitoring and Computing Abstracts, p. 471 (2002).

Chan, K.W., et al.; "17.3: Adaptive Reduction of Motion Artifact from Photoplethysmographic Recordings using a Variable Step-Size LMS Filter," IEEE, pp. 1343-1346 (2002).

Yamaya, Yoshiki, et al.; "Validity of pulse oximetry during maximal exercise in normoxia, hypoxia, and hyperoxia," J. Appl. Physiol., vol. 92, pp. 162-168 (2002).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Yoon, Gilwon, et al.; Multiple diagnosis based on Photoplethysmography: hematocrit, SpO2, pulse and respiration, Optics in Health Care and Biomedical optics: Diagnostics and Treatment; Proceedings of the SPIE, vol. 4916; pp. 185-188 (2002).

Tremper, K.K.; "A Second Generation Technique for Evaluating Accuracy and Reliability of Second Generation Pulse Oximeters," Journal of Clinical Monitoring and Computing, vol. 16, pp. 473-474 (2000).

Lopez-Silva, Sonnia Maria Lopez, et al.; "Near-infrared transmittance pulse oximetry with laser diodes," Journal of Biomedical Optics, vol. 8, No. 3, pp. 525-533 (Jul. 2003).

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Stetson, Paul F.; "Determining Heart Rate from Noisey Pulse Oximeter Signals Using Fuzzy Logic," The IEEE International Conference on Fuzzy Systems, St. Louis, Missouri, May 25-28, 2003; pp. 1053-1058.

Aoyagi, Takuo; "Pulse oximetry: its invention, theory, and future," Journal of Anesthesia, vol. 17, pp. 259-266 (2003).

Lee, C.M., et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

A. Johansson; "Neural network for photoplethysmographic respiratory rate monitoring," Medical & Biological Engineering & Computing, vol. 41, pp. 242-248 (2003).

Lopez-Silva, S.M., et al.; "Transmittance Photoplethysmography and Pulse Oximetry With Near Infrared Laser Diodes," IMTC 2004—Instrumentation and Measurement Technology Conference, Como, Italy, May 18-20, 2004; pp. 718-723.

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," Proceedings of the 26th Annual International conference of the IEEE EMBS, San Francisco, California, Sep. 2004, pp. 2153-2156.

Matsuzawa, Y., et al.; "Pulse Oximeter," Home Care Medicine, pp. 42-45 (Jul. 2004); (Article in Japanese—contains English summary of article).

Crespi, F., et al.; "Near infrared oxymeter prototype for non-invasive analysis of rat brain oxygenation," Optical Sensing, Proceedings of SPIE, vol. 5459, pp. 38-45 (2004).

Yan, Yong-sheng, et al.; "Reduction of motion artifact in pulse oximetry by smoothed pseudo Wigner-Ville distribution," Journal of NeuroEngineering and Rehabilitation, vol. 2, No. 3 (9 pages) (Mar. 2005).

F. Jaillon, et al.; "Diffusing-wave spectroscopy from head-like tissue phantoms: influence of a non-scattering layer," *Optics Express*, vol. 14, No. 22; Oct. 2006, pp. 10181-10194.

G. Dietsche, et al.; "Fiber-based multispeckle detection for time-resolved diffusing-wave spectroscopy: characterization and application to blood flow detection in deep tissue," *Applied Optics*, vol. 46, No. 35; Dec. 2007, pp. 8506-8514.

J. Huang, et al.; "Low Power Motion Tolerant Pulse Oximetry," Abstracts, A7, p. S103. (undated).

P. Lang, et al.; "Signal Identification and Quality Indicator™ for Motion Resistant Pulse Oximetry," Abstracts, A10, p. S105. (undated).

Hamilton, Patrick S., et al.; "Effect of Adaptive Motion-Artifact Reduction on QRS Detection," Biomedical Instrumentation & Technology, pp. 197-202 (undated).

Kim, J.M., et al.; "Signal Processing Using Fourier & Wavelet Transform," pp. II-310-II-311 (undated).

R. Neumann, et al.; "Fourier Artifact suppression Technology Provides Reliable SpO2" Abstracts, A11, p. S105. (undated).

Odagiri, Y.; "Pulse Wave Measuring Device," Micromechatronics, vol. 42, No. 3, pp. 6-11 (undated) (Article in Japanese—contains English summary of article).

J.M. Tualle, et al.; "Time-Resolved Diffusing Wave Spectroscopy for selected photon paths beyond 300 transport mean free paths," White Paper (undated).

Yamazaki, Nakaji, et al.; "Motion Artifact Resistant Pulse Oximeter (Durapulse PA 2100)," Journal of Oral Cavity Medicine, vol. 69, No. 4, pp. 53 (date unknown) (Article in Japanese—contains English summary of article).

International Search Report PCT/US2009/056952, 6 pages, mailed Apr. 20, 2010.

\* cited by examiner

SYSTEM AND METHOD FOR PHOTON DENSITY WAVE PULSE OXIMETRY AND PULSE HEMOMETRY

BACKGROUND

This section is intended to introduce the reader to various aspects of art that may be related to various aspects of the present embodiments, which are described and/or claimed below. This discussion is believed to be helpful in providing the reader with background information to facilitate a better understanding of the various aspects of the disclosed embodiments. Accordingly, it should be understood that these statements are to be read in this light, and not as admissions of prior art.

Pulse oximetry may be defined as a non-invasive technique that facilitates monitoring of a patient's blood flow characteristics. For example, pulse oximetry may be used to measure blood oxygen saturation of hemoglobin in a patient's arterial blood and/or the patient's heart rate. Specifically, these blood flow characteristic measurements may be acquired using a non-invasive sensor that passes light through a portion of a patient's tissue and photo-electrically senses the absorption and scattering of the light through the tissue. Typical pulse oximetry technology currently utilizes two light emitting diodes (LEDs) and a single optical detector to measure pulse and oxygen saturation of a given tissue bed.

A typical signal resulting from the sensed light may be referred to as a plethysmograph waveform. Such measurements are largely based on absorption of emitted light by specific types of blood constituents. Once acquired, this measurement may be used with various algorithms to estimate a relative amount of blood constituent in the tissue. For example, such measurements may provide a ratio of oxygenated to deoxygenated hemoglobin in the volume being monitored. It should be noted that the amount of arterial blood in the tissue is generally time varying during a cardiac cycle, which is reflected in the plethysmographic waveform.

The accuracy of blood flow characteristic estimation via pulse oximetry depends on a number of factors. For example, variations in light absorption characteristics can affect accuracy depending on where the sensor is located and/or the physiology of the patient being monitored. Additionally, various types of noise and interference can create inaccuracies. For example, electrical noise, physiological noise, and other interference can contribute to inaccurate blood flow characteristic estimates. Some sources of noise are consistent, predictable, and/or minimal, while some sources of noise are erratic and cause major interruptions in the accuracy of blood flow characteristic measurements. Accordingly, it is desirable to enable more accurate and/or controlled measurement of physiologic parameters by providing a system and method that addresses inconsistencies in physiologic characteristics of patients and issues relating to noise.

BRIEF DESCRIPTION OF THE DRAWINGS

Advantages of present embodiments may become apparent upon reading the following detailed description and upon reference to the drawings in which.

DETAILED DESCRIPTION OF SPECIFIC EMBODIMENTS

Figure 1:
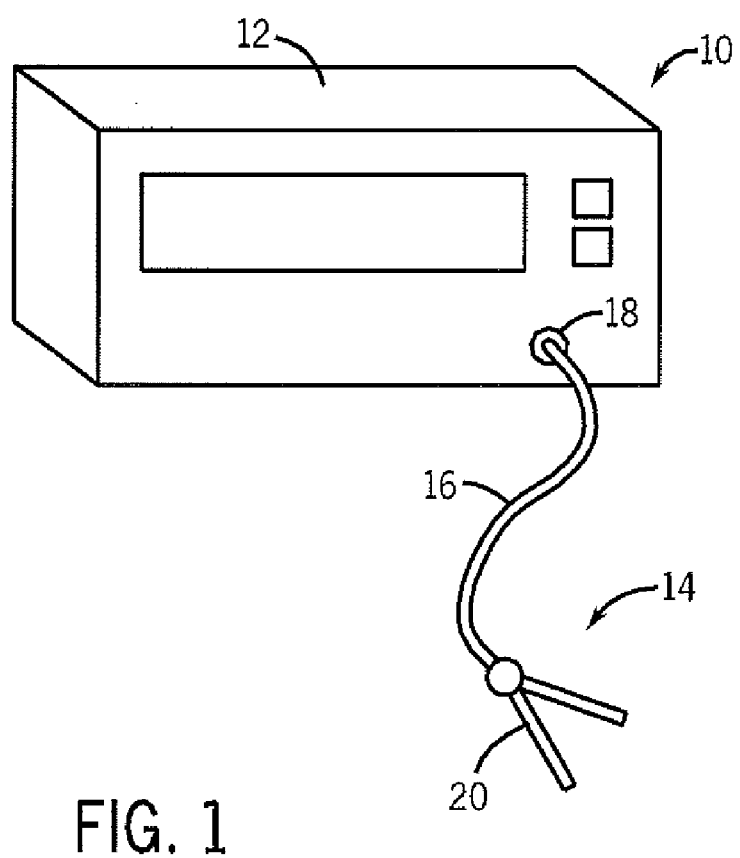
FIG. 1 illustrates a perspective view of a pulse oximeter system in accordance with present embodiments.

Present embodiments relate generally to medical devices. More particularly, present embodiments relate to estimating physiological parameters related to blood in a patient based on detection of light wave characteristics after the associated light waves have been transmitted through the patient's tissue.

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to non-invasively measuring physiologic parameters corresponding to blood flow in a patient by emitting light into a patient's tissue with light emitters (e.g., lasers/LEDs) and photoelectrically detecting the light after it has passed through the patient's tissue. More specifically, present embodiments are directed to modulating the emitted light at high frequencies to generate resolvable photon density waves. Photon density waves may be described as progressively decaying waves of intensity. On a microscopic level, photons generated by a light source generally make random migrations in a scattering medium. However, the photons collectively form a photon density wave at a modulation frequency that moves away from the light source. Photon propagation is generally dictated by scattering and absorption in the medium through which the waves are moving. Like other waves, photon density waves undergo refraction, diffraction, interference, dispersion, attenuation, and so forth.

Phase changes and amplitude changes in the photon density waves after passing through a medium may be detected to facilitate measurement of changes in total scattering particles and absorber concentration, respectively, in the observed medium. Indeed, the phase of such waves may be sensitive to scattering and the amplitude of such waves may be sensitive to absorption. For example, detection of phase changes in the photon density waves generated by modulation at high frequency may correspond to total hemoglobin because the distance between waves may be shorter than an average absorption length of photons. Thus, detected variations in the phase may be predominantly due to the scattering coefficient and not absorption. In other words, the variation in phase may be predominantly due to the total number of scattering particles (e.g., total hemoglobin) in the observed medium and not merely a ratio of particles (e.g., oxygenated and deoxygenated hemoglobin) that absorb different frequencies of light. On the other hand, changes in the amplitude of the photon density waves may correspond to absorption of specific light frequencies (e.g. red or infrared light) in the observed volume, and, thus, a ratio of different types of particles (e.g., oxygenated and deoxygenated hemoglobin) in the probed medium.

In addition to the features set forth above, it should also be noted that present embodiments may relate to emitting multiple high frequency photon density waves in coordination with one another to focus on certain tissue areas (e.g., regions rich with pulsatile signals), to facilitate identification of noise artifacts, to address patient specific tissue characteristics (e.g., skin color and low blood oxygen saturation levels), and/or to reduce noise in general. For example, multiple photon density waves may be emitted in patterns such that the waves build on one another to focus intensity at certain points throughout a tissue bed. In a specific example, a tissue bed may be swept with combinations of emission frequencies to identify areas rich with pulsatile signals. Similarly, waves may be emitted such that the waves cancel one another out in a substantially noise-free environment. Thus, detection of the waves that have not been canceled out may be indicative of the presence of noise. Additionally, relative measurements may be utilized to identify and/or correct noise. For example, certain wave features may be detected at multiple detector locations and compared to one another to identify characteristics such as venous pulsation noise.

FIG. 1 illustrates a perspective view of a pulse oximetry system 10 in accordance with some embodiments. The system 10 includes a pulse oximeter or monitor 12 that communicatively couples to a sensor 14. The monitor 12 may include a display, a tangible computer-readable medium (e.g., a memory, a floppy disk, or a CD), a processor, and various monitoring and control features. The sensor 14 may include a sensor cable 16, a connector plug 18, and a sensor assembly or body 20 configured to attach to a patient (e.g., a patient's finger, ear, forehead, or toe). The system 10 may be utilized to observe the blood constituents of a patient's arterial blood to facilitate estimation of the state of oxygen exchange in the patient's body by emitting waves into tissue and detecting the waves after dispersion and/or reflection by the tissue. The amount of light that passes through the tissue and other characteristics of light waves may vary in accordance with the changing amount of certain blood constituents in the tissue and the related light absorption and/or scattering. For example, as with conventional pulse oximeter systems, the system 10 may emit light from two or more LEDs or lasers into pulsatile tissue and then detect the transmitted light with a light detector (e.g., a photodiode or photo-detector) after the light has passed through the pulsatile tissue. Such measurements may be utilized to estimate a percentage of blood oxygen saturation in the probed volume of blood. Additionally, in accordance with present embodiments, the system 10 may modulate the emitted light to generate photon density waves at a high frequency such that phase shifts may be detected that correlate predominantly to scattering particles in the probed volume of blood.

As generally indicated above the system 10 may generate and detect light waves to facilitate non-invasive measurement of a patient's physiological characteristics. In embodiments, the system 10 may generate resolvable photon density waves and make relative measurements of certain detected wave characteristics after the waves have passed through a medium (e.g., a patient's tissue). The wave characteristics that may be measured in accordance with present embodiments may include characteristics that relate predominantly to absorption of the emitted light in the probed medium (e.g., amplitude change) and characteristics that relate predominantly to scattering in the probed medium (e.g., phase shift). It should be noted that, as will be discussed further below, the correlation of certain wave characteristic (e.g., amplitude and phase) measurements to certain medium characteristics (e.g., quantity of scattering particles and blood oxygen saturation) may be based on high frequency modulation of the system's light sources, which generate the resolvable photon density waves.

As indicated above, the system 10 may be utilized to make measurements that relate predominantly to scattering in the observed volume. More specifically, the system 10 may be utilized to make measurements relating to a total amount of scattering particles in the observed volume based on phase shifts detected in the emitted light waves. For example, the system 10 may emit light that is modulated at a high frequency (e.g., 50 MHz to 3.0 GHz) to generate resolvable photon density waves, and then measure the phase shift of these high frequency waves to facilitate estimation of a total number of scattering particles in the observed medium. Similarly, as set forth above, the system 10 may be utilized to make measurements that relate predominantly to absorption in an observed volume. For example, the system 10 may detect changes in AC and DC amplitudes of the resolvable photon density waves to facilitate detection of a ratio of certain constituents in the blood (e.g., a ratio of oxygenated to deoxygenated hemoglobin). It should be noted that the amplitude changes and phase shifts measured at a detection point may be considered relative to one or more points. For example, the amplitude and phase shifts measured at a detector may be considered relative to the associated values generated at the emitter.

Figure 2:
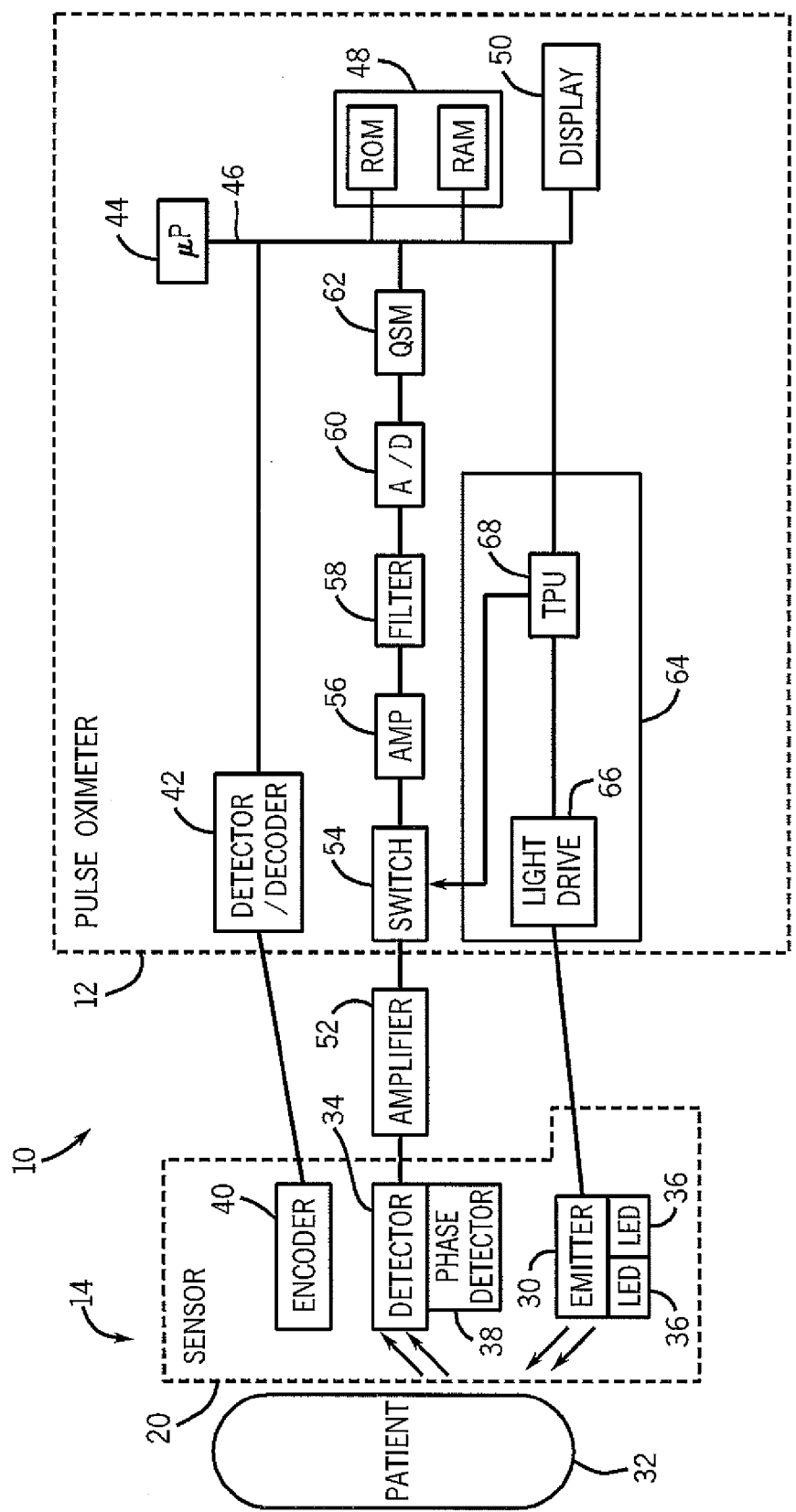
FIG. 2 illustrates a block diagram of a pulse oximeter system in accordance with present embodiments.

FIG. 2 is a block diagram of an embodiment of the pulse oximeter system 10 that may be configured to implement the embodiments of the present disclosure. As indicated above, the system 10 may include a monitor 12 and a sensor 14. The sensor 14 may be configured such that light from an emitter 30 can pass into a patient's tissue 32 when properly attached. Further, the sensor 14 may be configured such that after passing through the tissue 32, the dispersed light may be received by a photo-detector 34. The photo-detector 34 may then convert the received light into a photocurrent signal, which may then be provided to the monitor 12. It should be noted that in some embodiments, multiple sensors 14 may be employed. Further, in some embodiments, one or more sensors may each include multiple emitters and/or detectors. If multiple emitters are employed, it will generally be desirable for each of the emitters to include red and infrared (IR) light sources, such as LEDs 36, wherein each red and IR light source is configured to emit a wavelength that is within 10-20 nm of the other red or IR light source, respectively.

In some embodiments, in addition to the emitter 30 and the detector 34, the sensor assembly or body 20 may also contain various other features in accordance with present embodiments. For example, the sensor 14 may include a phase detector 38 capable of detecting phase shifts in photon density waves observed by the detector 34. While the phase detection feature 34 is positioned within the sensor assembly 20 in the illustrated embodiment, in some embodiments, the phase detection feature 34 may be located within the oximeter 12. Additionally, the sensor 14 may include an encoder 40 (e.g., a resistor or chip) which may be capable of providing signals indicative of the wavelength(s) of light received from the emitter 30 to allow the oximeter 12 to select appropriate calibration coefficients for calculating oxygen saturation. The data or signal from the encoder 40 may be decoded by a detector/decoder feature 42 in the oximeter 12.

In some embodiments, the oximeter 12 may include a microprocessor 44 coupled to an internal bus 46. Also connected to the bus 46 may be a memory 48 (e.g., RAM and/or ROM) and a display 50. Received signals from the detector 34 may be passed through a first amplifier 52, a switch 54, an analog multiplier 56, a low pass filter 58, and/or an analog-to-digital converter 60. The digital data may then be stored in a queued serial module (QSM) 62 for later downloading to the memory 48 as the QSM 62 fills up. In an embodiment, there may be multiple parallel paths of separate amplifier, filter, and A/D converters for multiple light wavelengths or spectra received, and/or for phase data generated by the phase detector 38. In one embodiment, a signal from the phase detector 38 may be processed in any suitable manner, and may be sent through a different data path than the signal from the detector 34, which may be configured to detect amplitude of the photon density waves. The received optical signal may be converted into an electrical signal at the detector 34. The electrical signal may then be amplified by the amplifier 52 and sent to a frequency mixer or analog multiplier (e.g., analog multiplier 56) to generate a signal that is proportional to a phase difference between a reference oscillator (not shown) and the received signal. Similarly, the AC and DC amplitudes of the received signal may be determined with peak detection circuits and low pass filters (e.g., filter 58).

As illustrated in the embodiment of FIG. 2, the emitter 30 may include the two LEDs 36. The LEDs 36 may receive modulated drive signals from the monitor 12 that activate the LEDs 36 and cause them to emit light at certain intervals. Thus, the monitor 12 may activate and deactivate the LEDs 36 at high frequencies that may facilitate measurements relating to scattering in the probed medium based on phase changes in emitted photon density waves. This modulation function may be performed by a modulator 64. The modulator 64 may include a hardware feature, a software feature, or some combination thereof. For example, a portion of the modulator 64 may be stored on the memory 48 and may be controlled by the processor 44. In the illustrated embodiment the modulator 64 includes a light driver 66 and a time processing unit (TPU) 68 that cooperate to modulate the light emissions of the LEDs 36. The TPU 68, which may include a sine wave generator, may provide timing control signals to the light drive circuitry 66, which controls when the emitter 30 is activated, and if multiple light sources are used, the multiplexed timing for the different light sources. The TPU 68 may also control the gating-in of signals from the detector 34 through the first amplifier 52 and the switching circuit 54. These signals are sampled at the proper time, depending at least in part upon which of multiple light sources is activated, if multiple light sources are used.

In the illustrated embodiment, the modulator 64 is disposed in the monitor 12. However, in some embodiments the modulation function may be performed by a modulator disposed within the sensor 14. Indeed, it should be noted that in some embodiments, the features related to modulating and detecting the phase of the emitted light waves may be arranged within the system 10 to avoid potential interference. For example, high frequency modulation and detection features may be co-located within the sensor 14 to reduce the distance traveled by the signals, and, thus, reduce potential interference. Indeed, in a specific example, the sensor 14 may include a commercially available chip set for phase measurement and commonly available drive circuits (e.g., DVD R/W driver circuits) for high frequency modulation. Examples of such devices may include the AD8302 available from Analog Devices™ and the LNH6525 available from National Semiconductor™. In other embodiments the LEDs 36 may be positioned within the monitor 12 and light may be transmitted from the LEDs 36 in the monitor 12 to the sensor 14 via fiber optics to reduce potential interference.

Regardless of the modulator's location, in contrast to traditional pulse oximetry, which conducts measurements at sufficiently low frequencies (e.g., 1.5 KHz) to be considered DC, the modulator 64 may be configured to modulate the LEDs 36 at sufficiently high frequencies (e.g., approximately 50 MHz to 3.0 GHz) to cause resolvable photon density waves to propagate through the tissue 38. In some embodiments, the modulator 64 may be configured to sweep a range from 50 MHz to 2.4 GHz. In some embodiments, the modulator 64 may be configured to modulate between 100 MHz and 1 GHz or to sweep a range from 100 MHz to 1 GHz. Thus, present embodiments operate at much higher frequencies than the traditional pulse oximetry sampling frequency of 1 sample every 67 microseconds.

In some embodiments, for continuous modulation of the LEDs 36, resolvable amplitude and phase relationships of the photon density waves may be established at various positions from the emitter along the tissue bed 32. By modulating the light emitters at sufficiently high frequencies, the distance between photon density waves may be shorter than the average distance required for light to be absorbed. Thus, the phase changes in the photon density waves can be attributed predominantly to scattering and not absorption. Further, in view of this, it can be determined that detected phase changes correspond to a number of scattering particles in the probed medium. The frequency of the photon density waves is essentially locked to the initial light source input and the phase change is essentially locked to arterial pulsation and the introduction of scattering particles. Indeed, the variation in AC scattering to DC scattering measured by phase offset may yield information about the total arteriole volume probed.

For a modulation frequency where the product of the frequency and the mean time between absorption events is much larger than 1, the change in phase between two points located a distance r from each other on a tissue bed may be given by the relation, $$\Delta\phi = r\sqrt{\frac{\omega\mu'_s}{6c}},$$

where c is the speed of light, $\omega$ is the angular frequency of modulation, and $\mu'_s$ is the reduced scattering coefficient. The reduced scattering coefficient for a tissue bed is comprised of both blood and surrounding tissue components. It can be written as, $$\mu'_s\text{total} = V_{blood}\mu'_s\text{blood} + V_{tissue}\mu'_s\text{tissue}.$$

The time varying component of this equation at a single wavelength will generally be only the portion due to arterial blood. The time varying component of this equation at a second wavelength will allow for the deconvolution of the scattering coefficient. The scattering coefficient for blood is related to the hematocrit (HCT) through the relation, $$\mu'_s\text{blood} = \sigma_s(1-g)(HCT/V_1)(1-HCT)(1.4-HCT),$$

where g is the anisotropy factor, $\sigma$ is the scattering cross section of an erythrocyte, Vi is the volume of an erythrocyte and HCT is the hematocrit.

Accordingly, when the modulator 64 operates at a high enough frequency, measured phase changes in the photon density waves may be utilized to calculate a number of scattering particles in the observed volume. For example, the monitor 12 may be configured to receive phase shift and/or amplitude data from the sensor 14 and calculate a value related to a quantity of scattering particles in the probed tissue for display on the monitor 12. Specifically, the monitor 12 may include instructions or an algorithm stored on the memory 48 and configured to perform such calculations.

Figure 3A:
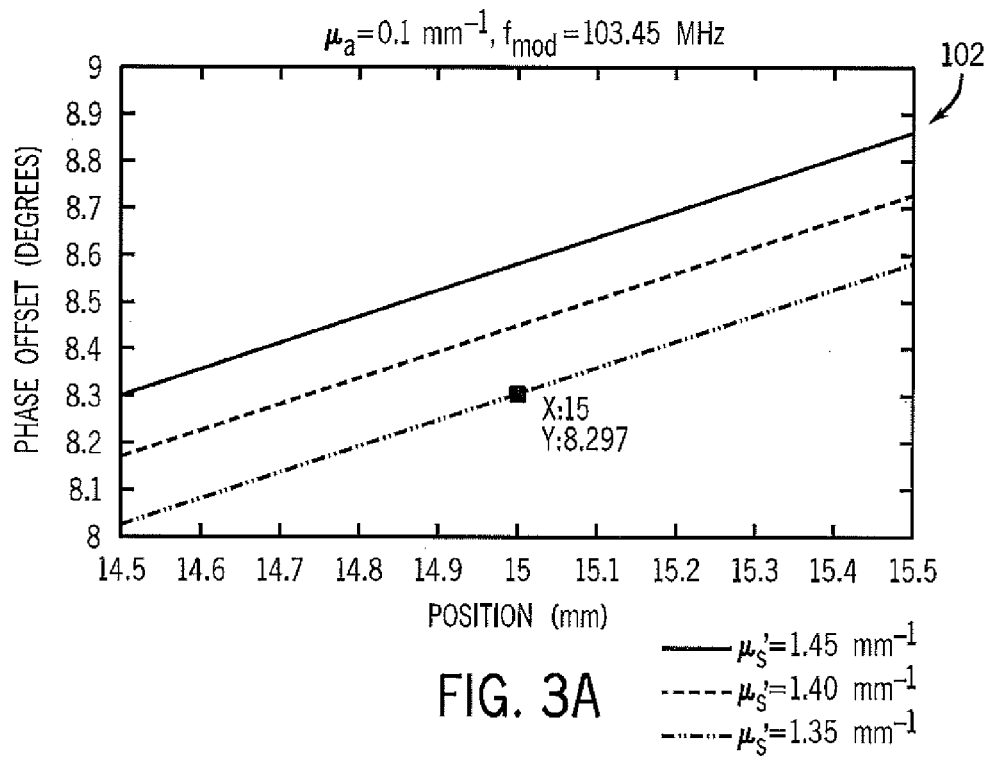
FIG. 3 illustrates a pair of graphs that represent simulations of phase changes in photon density waves modulated at high frequency, wherein the phase changes are due to scattering in accordance with present embodiments.
Figure 3B:
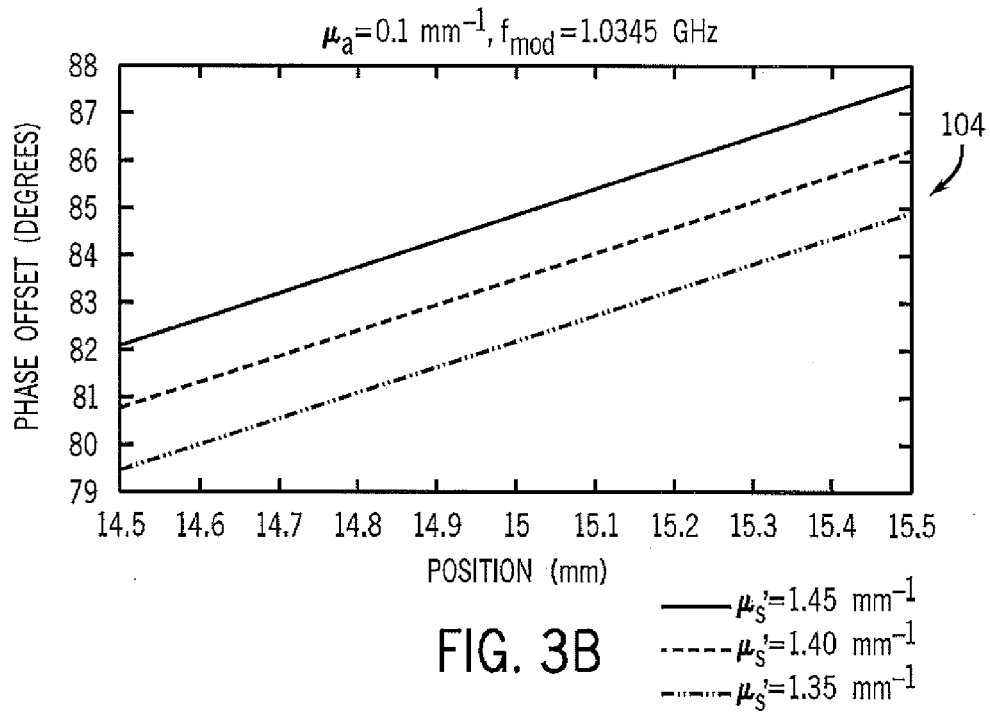

As an example of the correlation of phase change measurements of photon density waves modulated at high frequency to a number of scattering particles in the probed medium, FIG. 3 includes a pair of graphs that represent simulations of phase changes due to scattering at two different frequencies. Specifically, FIG. 3 includes a first graph 102 and a second graph 104 that represent simulations of phase change (measured in degrees) due to scattering variation of an arterial pulse (Hemoglobin 15 g/dL) for photon density waves at 890 nm that are modulated with a frequency of 103.4 MHz and 1.034 GHz, respectively. It should be noted that the increase in frequency from 103.4 MHz in the first graph 102 to 1.034 GHz in the second graph 104 results in a phase change of approximately 3-4 degrees. This change correlates to the reduction in distance between the wave fronts of the photon density waves. In other words, because the distance between waves is reduced even further from the 103.4 M modulation rate (first graph 102) to the 1.034 GHz modulation rate (second graph 104) and there is less opportunity for absorption, the phase change of the higher modulation rate corresponds more specifically to scattering. In some embodiments, a range of frequencies between those shown in FIGS. 3 and 4 may be swept through to profile the characteristics of the tissue at different photon density wave frequencies.

Scattering may be quantified based on phase change. Specifically, as set forth above, a modulation frequency where the product of the frequency and the mean time between absorption events is much larger than 1, the change in phase between two points may be given by the relation, $$\Delta\phi = r\sqrt{\frac{\omega\mu'_s}{6c}}.$$

Changes in phase due to arterial pulsation may be directly related to the change in scattering coefficient of the medium which is due to the change in the concentration of the number of erythrocytes. It should be noted that a second method for correlating the scattering changes from the phase could involve a calibration curve determined from tissue phantoms or clinical data.

Figure 4:
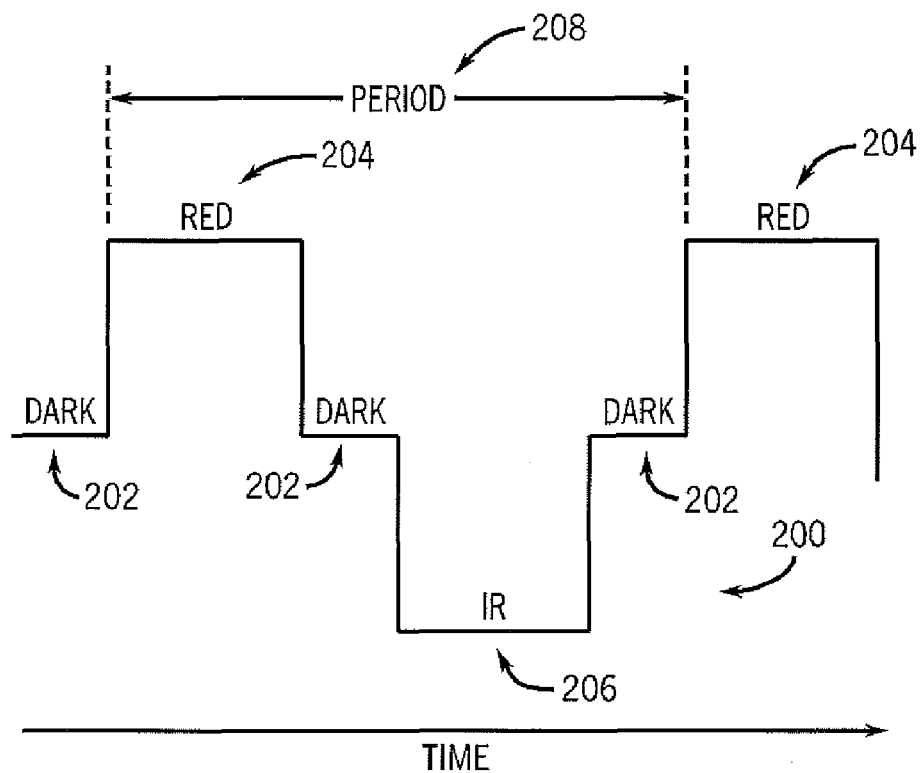
FIG. 4 illustrates an example of a source modulation signal in accordance with present embodiments.

FIG. 4 illustrates an example of a source modulation signal as driven by cross-coupled LEDs in accordance with some embodiments. Specifically, FIG. 4 illustrates a control signal 200 that may be generated by the modulator 64 to activate and/or deactivate an emitter including red and IR light sources, such as the LEDs 36. In other embodiments, separate modulators may be utilized for each light source and/or additional light sources. Indeed, when multiple emitters are utilized, each emitter may be modulated by a separate modulator.

In the illustrated embodiment, the control signal 200 is representative of dark intervals 202, intervals of power 204 being supplied to a red LED, and intervals of power 206 being supplied to an IR LED over time. Further, the control signal 200 has a period designated by reference number 208. This period 208 may be adjusted such that each of the LEDs 36 may be modulated with a desired frequency (e.g., approximately 100-1000 MHz) to generate photon density waves. Such adjustments to the modulation frequency may facilitate detection of phase shifts in the photon density waves, and, thus, variations in scattering based on such phase shifts. As may be appreciated by those of ordinary skill in the art the control signal 200 may be adjusted or modified for different scenarios. For example, the control signal 200 may be adjusted to be generally sinusoidal, adjusted to include various intensity levels, and so forth. The sinusoidal nature of the wave may be controlled by a wave generator and the intensity levels may be adjusted by providing more power and/or by reducing dark intervals and increasing the length of time that light is emitted.

As indicated above, the phase of the photon density waves may be sensitive to changes in the scattering coefficient, while the amplitude of the photon density waves may be sensitive to the concentration of absorbers in the medium. Specifically, with regard to amplitude measurements, the AC amplitude and DC amplitude may yield information about absorption in the volume. Thus, detection of amplitude changes in the photon density waves may be utilized to calculate absorber concentration values in the observed medium, such as blood oxygen saturation values. Such calculations may be made using the standard ratio of ratios (i.e., ratrat) technique for the constant and modulated values of the photon density wave amplitudes at two wavelengths. Once the ratio of ratios values is obtained, it may be mapped to the saturation from clinical calibration curves.

With regard to phase shift measurements, when the wavelength of the photon density waves get below that of the mean absorption coefficient, the phase becomes almost exclusively a function of the scattering coefficient. While dependent upon the tissue bed being probed, this is generally believed to occur at a modulation frequency in the range of approximately 500 MHz. Thus, the phase shift measurement may yield information about the number of erythrocytes or red blood cells in the local probed volume. The HCT discussed above is proportional to the number of erythrocytes. Accordingly, by sweeping frequencies, a multi-parameter output may be obtained that relates to standard pulse oximetry measurements as well as the puddle hematorcit.

The amplitude and phase at a given frequency may be proportional to the scattering and absorption coefficient at a given wavelength until the product of the frequency and the mean time between absorption events is much larger than 1. When the product of the frequency and the mean time between absorption events is much larger than 1, the amplitude is a function of the absorption and phase is only a function of the scattering. Thus, a frequency sweep may be used to reduce the error in the determination of a single value of reduced scattering coefficient for the blood and a single value of absorption coefficient. Indeed, in some embodiments, the amplitude and phase information may be utilized together to yield a value of total hemoglobin per unit volume.

In some embodiments, by modulating the light sources at a sufficient frequency, and, thus, facilitating a detectable phase shift that corresponds to scattering particles, present embodiments may provide an extra degree of certainty for blood flow parameter measurements. Indeed, the detected amplitude for the photon density waves may be utilized to calculate traditional pulse oximetry information and the phase may be utilized to confirm that such values are correct (e.g., within a certain range of error). For example, the amplitude information may be utilized to calculate a blood oxygen saturation ($SpO_2$) value and empirical data may indicate that a particular $SpO_2$ value should correspond to a particular phase variation at a given frequency. In other words, there may be a certain phase change that should accompany a given increase in absorber observed as a change in amplitude. Various algorithms (e.g., learning based algorithms such as support vector machines, cluster analysis, neural networks, and PCA) based on the measured phase shift and amplitude change may be compared to determine if the amplitude shift and phase shift correlate to a known $SpO_2$. If both the measured amplitude shift and phase shift correlate to a known $SpO_2$, the measured $SpO_2$ value may be deemed appropriate and displayed or utilized as a correct $SpO_2$ value. Alternatively, if the measured amplitude shift and phase shift do not agree, the calculated $SpO_2$ value may be identified as being corrupt or including too much noise and, thus, be discarded.

Figure 5:
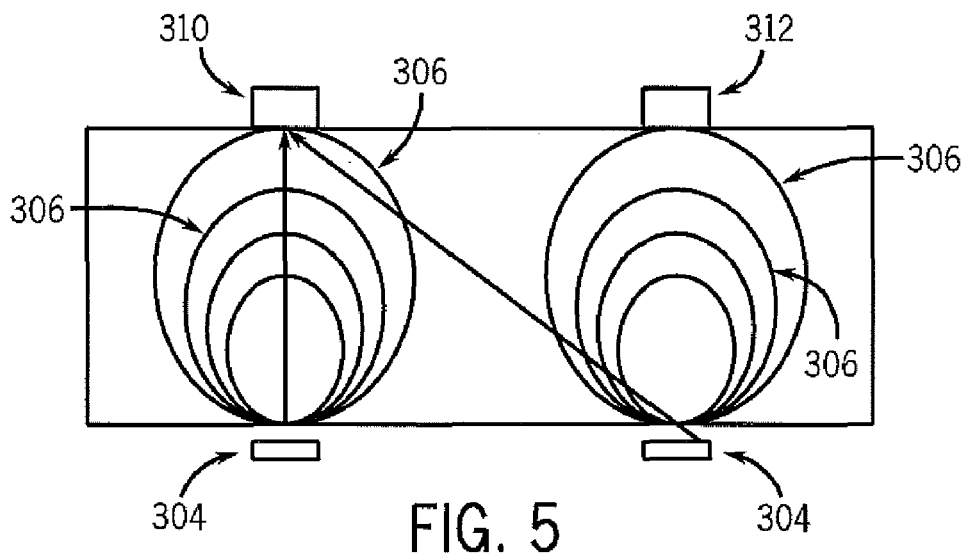
FIGS. 5-7 include representative diagrams of a multiple emitter and/or detector arrangements being utilized in conjunction with one another in accordance with present embodiments.
Figure 6:
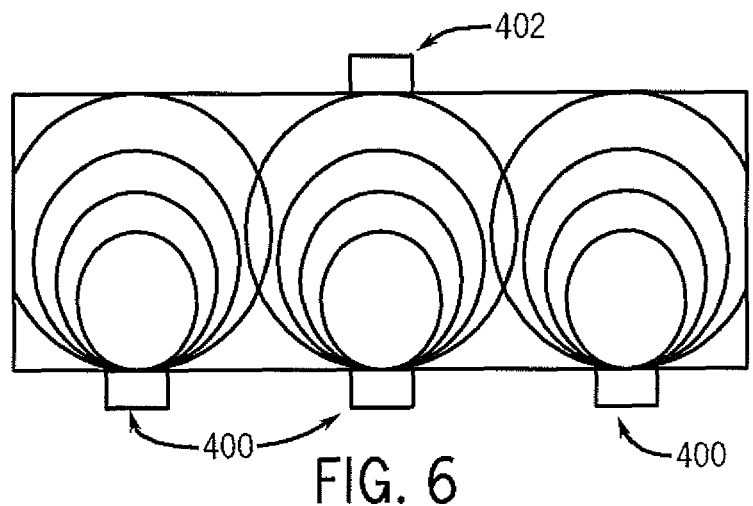
Figure 7:
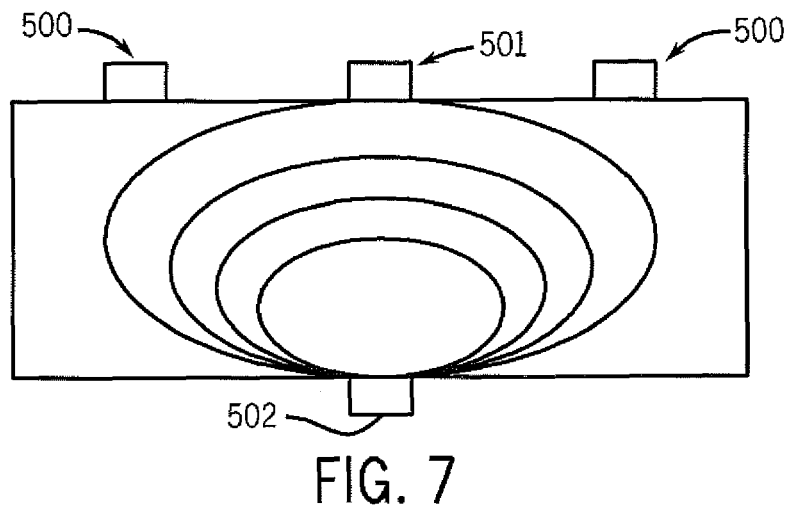

In some embodiments, as illustrated by FIGS. 5-7, multiple emitter and/or detector arrangements may be utilized in conjunction with one another. Specifically, FIG. 5 illustrates a first emitter 302 and a second emitter 304, wherein each of the emitters 302, 304 includes a red and an IR light source (e.g., LED). Waves 306 represent photon density waves propagating through tissue from the emitters 302, 304 to a first detector 310 and a second detector 312. As will be understood by one of ordinary skill in the art, because the multiple emitters are generating separate waves in the same tissue bed, the waves can be made to interfere with one another by adjusting the modulation frequencies of each emitter 302, 304. Accordingly, multiple emitters may be utilized to steer intensities through the tissue and adjust intensity patterns in the tissue. For example, the phase of the photon density waves could be adjusted in such a way as to completely cancel out any signal at the first detector 310. Thus, if the first detector 310 detects a signal, it may be an indication of noise.

FIG. 6 illustrates an embodiment including multiple emitters 400 and a single detector 402. This embodiment may be utilized to generate an adaptive constructive/destructive interference pattern in the tissue bed by adjusting the relative phases of the emitters (at a given wavelength) that would allow for the measurement of local tissue components. These would be visible in the phase and amplitude changes determined by the single detector.

In other embodiments utilizing multiple emitters, the interference of photon density waves may facilitate sweeping photon density waves through a probed volume by changing the relative phase between the emitters. For example, such techniques may be utilized to establish a "phased array" of photon density waves for use in pulse oximetry and hemometry techniques. Indeed, such a "phased array" technique may facilitate identification of regions rich with pulsatile signals in the probed tissue and/or calibration of a sensor through the interference of photon density waves. For example, the phases of individual waves may be controlled to determine the intensity profile within the medium.

It may be desirable to detect regions rich with pulsatile signals to facilitate obtaining a strong pulsatile signal. For example, it may be desirable to focus on a specific location in tissue that includes an artery or even a specific portion of the artery. Periodic sweeps may be performed to insure that the focus remains on the pulsation-rich regions. Further, such a technique may define an adaptive measurement system that may be utilized to identify regions of low saturation and/or regions in the probed tissue where blockage may result in anemic conditions. Additionally, it is believed that the use of multiple emitters may facilitate adaptation of the sensor to different physiological variations between patients, such as different skin and/or tissue characteristics.

FIG. 7 illustrates an embodiment including multiple detectors 500 and a single emitter 502. This embodiment may be utilized to identify non-physiological artifact. Each of the multiple detectors 500 may have a different phase and amplitude relationship with respect to each other. Uncorrelated changes in phase and amplitude between the multiple detectors 500 would result in a non-physiological artifact such as noise artifact, sensor off, and so forth.

The inclusion of multiple detectors around a tissue bed may facilitate detection of and/or compensation for a variety of noise artifacts that typically plague existing pulse oximetry technologies. Indeed, for a given wavelength, a time-varying phase and amplitude relation between multiple detectors may be established which is correlated to arterial pulse. The phase and amplitude information may form a phase space that yields a bounded parameter space for a single wavelength that contains physiological measurements. Noise artifacts will typically lie outside of this bounded area, as will be discussed in further detail below. Further, the addition of a second wavelength may facilitate formation of a 4-dimensional physiological measurement space that facilitates noise artifact reduction due to constraints of decision planes in the hyperspace. Correlated phase and amplitude changes for a single wavelength are bounded by physiological parameters such as arteriole density, realistic hematocrit numbers, and so forth. At a single wavelength, these bounds result in bounds on the detected amplitude and phase in a 2D space. These same bounds are applicable for a second wavelength. The 4 factor correlation (phase(wavelength1),phase(wavelength2), amplitude(wavelength1), amplitude(wavelength2)) is bounded by physiological factors in a linked 4D space. The bounds can be drawn as hyperplanes in that space. For example, cluster analysis, Neural Networks, and partial least squares (PLS) algorithms may be used to generate the decision planes and compensate for a variety of noise artifact.

Figure 8:
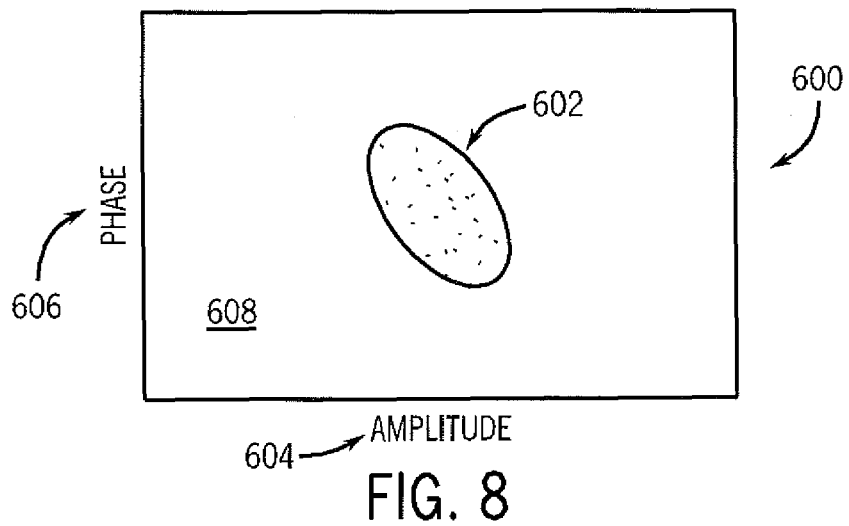
FIG. 8 illustrates a 2-dimensional plot that represents a physiological state characterized by amplitude and phase shifts in accordance with present embodiments.

In some embodiments, and as an example, FIG. 8 includes a 2-dimensional plot 600 that represents a physiological state 602 characterized by amplitude 604 and phase shifts 606. Once phase shift and/or amplitude data has been properly characterized based on empirical data, certain correlations may be indicative of a change in pressure (e.g., a sensor is attached too tightly), a certain area of tissue being subject to exsanguination, a sensor being off, noise being present, and so forth. The plot 600 is representative of a single wavelength at a given frequency. Thus, multiple wavelengths at a given frequency would each have this type of physiological space for expected amplitude and phase variation. Noise artifact 608 will generally lie outside of this bounded parameter space or physiological regime. Accordingly, if a measurement falls outside of the physiological regime, it may be discarded as including too much noise. When a measurement is discarded, it may be replaced with the previous measurement or some combination of historical values. For example, historical values may be averaged using an averaging routine to provide a replacement for the noisy current measurement value.

While the embodiments of the present disclosure may be susceptible to various modifications and alternative forms, specific embodiments have been shown by way of example in the drawings and will be described in detail herein. However, it should be understood that the present embodiments are not intended to be limited to the particular forms disclosed. Rather, present embodiments are to cover all modifications, equivalents and alternatives falling within the spirit and scope of present embodiments as defined by the following appended claims.

What is claimed is:

1. A monitoring system, comprising:
    an emitter configured to emit light into tissue;
    a modulator configured to modulate the light to generate photon density waves at a modulation frequency, wherein the modulation frequency is above about 50 MHz and below about 3 GHz;
a detector configured to detect relative characteristics of the photon density waves including amplitude changes and phase shifts;
a processor configured to make determinations relating to a value of a physiologic parameter of the tissue based on the phase shifts, and the processor is configured to reject or accept the determined value of the physiologic parameter based on whether calculations based on the relative characteristics are complimentary; and
a display feature configured to present the value of the physiologic parameter to a user.

2. The system of claim 1, wherein the modulator is configured to modulate the light at the modulation frequency above approximately 100 MHz and below approximately 1 GHz.

3. The system of claim 1, wherein the processor is configured to calculate an estimated number of scattering particles in the tissue based on detected phase shifts.

4. The system of claim 1, comprising a plurality of emitters, wherein the modulator is configured to modulate light from the plurality of emitters to sweep the tissue with a plurality of modulation frequencies.

5. The system of claim 1, wherein the modulator comprises a DVD R/W driver circuit.

6. The system of claim 1, comprising a plurality of emitters capable of establishing a phased array and a second calculation component configured to utilize the phased array to identify a region of the tissue rich with pulsatile signals or a region of the tissue with low saturation.

7. The system of claim 1, comprising a noise detection feature configured to identify noise artifacts based on a defined range of calculated values based on the amplitude changes and phase shifts.

8. The system of claim 1, wherein the modulator is configured to establish a phased array of photon density waves for use in pulse oximetry and hemometry techniques.

9. A method, comprising:
modulating light at a modulation frequency that is within a range between 100 MHz and 3 GHz to generate photon density waves in a medium;
detecting relative amplitude changes and phase shifts in the photon density waves;
calculating a value related to a number of scattering particles in the medium based on the phase shifts; and
detecting and graphically indicating a physiologic value related to the scattering particles in the medium based on the phase shifts.

10. The method of claim 9, comprising modulating multiple light emissions to generate a phased array of photon density waves.

11. The method of claim 10, comprising identifying regions rich with pulsatile signals based on the phased array of photon density waves.

12. The method of claim 9, comprising identifying regions of low saturation based on the phased array of photon density waves.

13. The method of claim 9, comprising sweeping the modulation frequency through a range from 500 MHz to 1 GHz.

14. A method, comprising:
emitting light from a plurality of light sources into a medium;
modulating the light from the plurality of light sources at different frequencies to generate photon density waves, wherein the different frequencies are approximately 100 MHz to 1 GHz;
coordinating the modulation of the plurality of light sources to establish coordinated wave characteristics;
identifying noise based on whether the coordinated wave characteristics are within a defined physiologic regime; and
calculating values for physiologic features of the medium based on detection of relative characteristics of the photon density waves after passing through the medium.

15. The method of claim 14, wherein the coordinated wave characteristics comprise focused wave intensity in a specified region of the medium.

16. The method of claim 14, comprising sweeping the medium with a plurality of modulation frequencies to facilitate calibration.

17. Application instructions stored on a tangible, non-transitory computer-readable medium, the application instructions comprising:
code configured to control modulation of light at a modulation frequency to generate photon density waves in a medium, wherein the modulation frequency is above about 100 MHz and below about 3 GHz;
code configured to facilitate detection of relative amplitude changes and phase shifts in the photon density waves;
code configured to calculate a value related to a number of scattering particles in the medium based on the phase shifts; and
code configured to identify and graphically indicate a physiologic value related to the scattering particles in the medium based on the phase shifts.

18. The application instructions of claim 17, comprising code configured to control modulation of multiple light emissions to generate a phased array of photon density waves.

19. A monitoring system, comprising:
an emitter configured to emit light into tissue;
a modulator configured to modulate the light to generate photon density waves at a modulation frequency, wherein the modulation frequency is above about 50 MHz and below about 3 GHz;
a detector configured to detect relative characteristics of the photon density waves including amplitude changes and phase shifts;
a processor configured to make determinations relating to a value of a physiologic parameter of the tissue based on the phase shifts, and the processor is configured to calculate an estimated number of scattering particles in the tissue based on detected phase shifts; and
a display feature configured to present the value of the physiologic parameter to a user.

20. A monitoring system, comprising:
an emitter configured to emit light into tissue;
a modulator configured to modulate the light to generate photon density waves at a modulation frequency, wherein the modulation frequency is above about 50 MHz and below about 3 GHz;
a detector configured to detect relative characteristics of the photon density waves including amplitude changes and phase shifts;
a noise detection feature configured to identify noise artifacts based on a defined range of calculated values based on the amplitude changes and phase shifts;
a processor configured to make determinations relating to a value of a physiologic parameter of the tissue based on the phase shifts; and
a display feature configured to present the value of the physiologic parameter to a user.

* * * * *